United States Patent [19]
Hamilton et al.

[11] Patent Number: 5,648,556
[45] Date of Patent: *Jul. 15, 1997

[54] SYNTHESIS OF BIS(2,2-DINITROPROPYL) ACETAL (BDNPA)

[75] Inventors: R. Scott Hamilton, Bear River City; Robert B. Wardle, Logan, both of Utah

[73] Assignee: Thiokol Corporation, Ogden, Utah

[ * ] Notice: The term of this patent shall not extend beyond the expiration date of Pat. No. 5,449,835.

[21] Appl. No.: 339,138

[22] Filed: Nov. 14, 1994

[51] Int. Cl.$^6$ .......................... C07C 41/50; C07C 43/30
[52] U.S. Cl. .............................................................. 568/590
[58] Field of Search .............................................. 568/590

[56] References Cited

U.S. PATENT DOCUMENTS 5,449,835  9/1995  Hamilton et al. ....................... 568/590

*Primary Examiner*—Gary Geist
*Assistant Examiner*—Dwayne C. Jones
*Attorney, Agent, or Firm*—Cushman Darby & Cushman IP Group of Pillsbury Madison & Sutro, LLP; Ronald L. Lyons, Esq.

[57] ABSTRACT

A nonsolvent process of synthesizing bis(2,2-dinitropropyl) acetal (BDNPA) is disclosed. In the process, 2,2-dinitropropanol (DNPOH) is reacted at low temperature with an acetaldehyde source in the presence of an acid catalyst, such as a Lewis acid catalyst or protic acid catalyst. To inhibit by product formation, the reaction temperature is maintained from about −30° C. to 30° C. Upon completion of the reaction, the reaction solution is quenched with water and washed with an aqueous hydroxide solution. The hydroxide concentration should be sufficient to neutralize any acid formed during the quenching step and to solubilize unreacted 2,2-dinitropropanol as well as other aqueous soluble byproducts in the reaction solution. The BDNPA product is extracted with methyl tert-butyl ether (MTBE) or equivalent solvent. The organic solvent is evaporated to yield usable BDNPA product. The resulting yield is at least 50% based on the starting quantity of 2,2-dinitropropanol.

20 Claims, No Drawings

SYNTHESIS OF BIS(2,2-DINITROPROPYL) ACETAL (BDNPA)

GOVERNMENT RIGHTS

The United States Government has a paid-up license in this invention and the right in limited circumstances to require the patent owner to license others on reasonable terms as provided for by the terms of contract No. DAAA21-94-D-0003 awarded by the U.S. Army.

FIELD OF THE INVENTION

The present invention relates to synthesis of bis(2,2-dinitropropyl)acetal (BDNPA) without the use of a solvent medium.

BACKGROUND OF THE INVENTION

Bis(2,2-dinitropropyl)acetal (BDNPA) is an energetic plasticizer used in propellant and explosive applications. BDNPA is often combined with more energetic, though chemically similar, bis(2,2-dinitropropyl)formal (BDNPF) in a 50:50 weight percent mixture. While BDNPF is a solid at room temperature, the mixture of BDNPF and BDNPA is a liquid. BDNPA/BDNPF is a commercialized product.

The current method for synthesizing BDNPA requires a methylene chloride solvent system. However, there is growing environmental concern about chlorinated solvents' potential contribution to ozone depletion and possible carcinogenic properties. Thus, it would be a significant advancement in the art to provide a method for synthesizing BDNPA which does not use chlorinated solvents.

In addition, the use of a solvent in a chemical manufacturing process adds the need for solvent separation and waste disposal procedures. For instance, it is believed the current BDNPA manufacturing process has a high temperature (about 125° C.) vacuum evaporation step to remove the methylene chloride solvent and minor volatile byproduct impurities. Such evaporation not only increases manufacturing costs, but also represents a safety hazard by subjecting energetic materials to high temperatures.

It will be appreciated that there is a need in the art for a process of synthesizing BDNPA which does not require the use of chlorinated solvents, and which avoids costly and dangerous evaporation procedures.

Such methods of synthesizing BDNPA are disclosed and claimed herein.

SUMMARY OF THE INVENTION

The present invention is directed to a process of synthesizing bis(2,2-dinitropropyl)acetal (BDNPA). In the process, 2,2-dinitropropanol (DNPOH) is reacted at low temperature with an acetaldehyde source in the presence of an acid catalyst. The reaction is shown below:

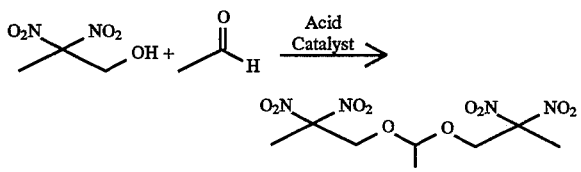

In the synthesis process, solid 2,2-dinitropropanol is mixed with an acetaldehyde source to form a reaction solution. A slight excess of the acetaldehyde source, such that more than one mole of acetaldehyde is present for every two moles of DNPOH, is preferably used in the reaction. Examples of typical acetaldehyde sources include acetaldehyde, paraldehyde, metaldehyde, and acetal. The acetaldehyde source generates acetaldehyde in situ for participation in the reaction with 2,2-dinitropropanol.

An acid catalyst is then slowly added to the reaction solution. Acid catalysts are preferably selected from Lewis acid catalysts and protic acid catalysts. During the addition, the reaction solution is preferably maintained at a temperature below 30° C. and agitated.

Upon completion of the reaction, the reaction solution is quenched with water. The water extracts the acid catalyst, water soluble reactants, and water soluble byproducts from the reaction solution. Methyl tert-butyl ether (MTBE) is added to extract the BDNPA product. Although other low boiling temperature polar organic solvent may be used to extract BDNPA, it has been found that MTBE is able to extract BDNPA at sufficiently high purity such that the BDNPA product is usable for military applications without further purification.

The reaction solution is then washed with an inorganic base solution, such as a hydroxide solution. Sufficient hydroxide is used to neutralize acid formed during the quenching step and to solubilize unreacted 2,2-dinitropropanol as the nitronate salt, as well as any other aqueous soluble byproducts in the reaction solution. During the hydroxide wash, the pH should preferably be kept sufficiently low to prevent hydrolysis of the BDNPA product. It is currently preferred to maintain the pH below 14 and preferably below 11. The exposure time and concentration of the inorganic base solution is preferably limited to prevent hydrolysis of the polar organic solvent or BDNPA product. It is important to note that the reaction solution may be washed with the inorganic base solution either before or after the polar organic solvent is added.

The aqueous phase is removed and discarded. The organic phase is washed with water. Finally, the organic solvent is evaporated to yield usable BDNPA product. The resulting yield is at least 50%, and preferably at least 60%, based on the starting quantity of 2,2-dinitropropanol. The evaporation is preferably accomplished at a temperature less than 60° C. and at a pressure less than about 150 mm Hg, and more preferably at a temperature less than 50° C. and at a pressure less than 20mm Hg. In simulated batch autoignition tests, an exotherm was observed at about 105° C. It is important that the evaporation occurs at low temperature, because there is the potential for an undesired exothermic reaction at higher temperatures.

DETAILED DESCRIPTION OF THE INVENTION

The present invention is directed to a process of synthesizing bis(2,2-dinitropropyl)acetal (BDNPA). In the process, 2,2-dinitropropanol (DNPOH) is reacted at low temperature with an acetaldehyde source in the presence of an acid catalyst.

In the synthesis process, 2,2-dinitropropanol is mixed with an acetaldehyde source to form a reaction solution. Typical acetaldehyde sources include acetaldehyde, paraldehyde, metaldehyde, and acetal. The acetaldehyde source generates acetaldehyde in situ for participation in the reaction with 2,2-dinitropropanol. The reaction is preferably carried out such that a slight stoichiometric excess of acetaldehyde is present.

An acid catalyst is then slowly added to the reaction solution. The acid catalyst is selected from Lewis acid catalysts and protic acid catalysts. Examples of typical Lewis acid catalysts include $BF_3$, $B_3$.etherate, $BCl_3$, $BBr_3$, $SnF_4$, $SnCl_4$, $SnBr_4$, $TiCl_3$, $TiCl_4$, $TiBr_3$, and $TiBr_4$. Examples of typical protic acid catalysts include $H_2SO_4$, HCl, $H_3PO_4$, and HBr. The acid catalyst participates in the reaction as a catalyst or dehydrating agent instead of a combinatorial reagent. That is, the acid catalyst does not combine with the 2,2-dinitropropanol or acetaldehyde source to form the final BDNPA product.

During the acid catalyst addition, the reaction solution is preferably agitated. To inhibit byproduct formation, the reaction temperature during the acid catalyst addition is preferably from about −30° C. to 30° C., more preferably from about −10° C. to 10° C., and most preferably from about −5° C. to 5° C. Although the BDNPA product is produced as the temperature increases, an increasing amount of undesirable byproducts are also produced. For this reason, the high temperatures are not preferred.

Upon completion of the reaction, the reaction solution is quenched with water. The water extracts the acid catalyst, water soluble reactants, and water soluble byproducts from the reaction solution.

The reaction solution is washed with an inorganic base solution, such as a hydroxide solution. The hydroxide concentration should be sufficient to neutralize acid formed during the quenching step and to solubilize unreacted 2,2-dinitropropanol as the nitronate salt, as well as any other aqueous soluble byproducts in the reaction solution. The pH during the inorganic base wash is preferably kept sufficiently low to prevent hydrolysis of the BDNPA product. It is currently preferred to balance the amount of base solution used with its concentration such that the pH is maintained below about 11 during the initial base solution wash. The pH may be higher in a second base solution wash, but is preferably kept below 14. The hydroxide concentration may range from 1% to 25%, by weight. The hydroxide solution can be prepared from a number of different hydroxide salts known in the art, such as NaOH, KOH, and LiOH. A 5%, by weight, NaOH solution is currently preferred.

Finally, the BDNPA product is extracted with a polar organic solvent which does not contain chlorine. Suitable solvents should have a boiling temperature below 125° C., preferably below 100° C., and most preferably below about 80° C., at ambient pressure. The organic solvent preferably does not react with the inorganic base under the exposure time and concentration conditions used in the process. It has been found that methyl tert-butyl ether (MTBE) is able to extract BDNPA at sufficiently high purity such that the BDNPA product is usable for military applications without further purification. It is important to note that the BDNPA product can be extracted from the reaction solution with the polar organic solvent either before or after the inorganic base washings.

The aqueous phase is removed and discarded. The organic phase is washed with water to remove any remaining water soluble byproducts or reactants. Finally, the organic solvent is evaporated to yield usable BDNPA product. The resulting yield is at least 50%, and preferably 60%, based on the starting quantity of 2,2-dinitropropanol. The evaporation is preferably accomplished at a temperature less than 60° C. and at a pressure less than about 150 mmHg, and more preferably at a temperature less than 50° C. and at a pressure less than 20 mm Hg.

As used herein, usable BDNPA product includes BDNPA of sufficient purity that a 50:50 mixture of BDNPA/BDNPF meets military density, refractive index and acid aging standards. The military specification for a 50:50 BDNPA/BDNPF mixture requires that the density be between 1.38–1.40 g/cc, the refractive index be between 1.462 and 1.464, and the acid aging test be below 0.5 mg KOH/g nitroplasticizer. In the acid aging text, the BDNPA nitroplasticizer is aged in an oven at 105° C. for 7 days. After aging, the sample is titrated with KOH to determine the acid content. The result is reported as mg KOH/g nitroplasticizer.

The following examples are offered to further illustrate the present invention. These examples are intended to be purely exemplary and should not be viewed as a limitation on any claimed embodiment.

EXAMPLE 1

Bis(2,2-dinitropropyl)acetal (BDNPA) was synthesized by mixing 2.00 g (13.4 mmole) 2,2-dinitropropanol (DNPOH) and 0.48 g (10.8 mmole) acetaldehyde in an empty, dry reaction vessel that had been purged with dry nitrogen. The DNPOH and acetaldehyde reaction solution was cooled to between 0° C. to 5° C. 0.96 g (0.86 ml, 6.8 mmole) of $BF_3.O(Et)_2$ were slowly added to the reaction solution over a 45 minute period. During the $BF_3.O(Et)_2$ addition, the reaction solution was cooled, stirred, and maintained under nitrogen atmosphere. The reaction was quenched with 4 ml of water. 10 ml of MTBE (methyl tert-butyl ether) were added to dissolve the BDNPA product. The aqueous layer was separated from the MTBE layer. The MTBE layer was washed with 5 weight percent NaOH solution to maintain pH 11 for one-half hour. The aqueous layer was again separated from the MTBE layer. The MTBE layer was washed a second time with the same amount of 5 weight percent NaOH used in the first wash, and the aqueous layer was separated. The MTBE layer was washed three times with 5 ml of water and dried with $MgSO_4$. The MTBE was evaporated at 40° C. and less than 20 mmHg, leaving 1.29 g (59% yield) BDNPA.

EXAMPLE 2

A scaled-up (12.5 pound) synthesis of bis(2,2-dinitropropyl)acetal was made as follows. A 5 gallon polypropylene bucket with a tight fitting lid was used as the reaction vessel. Holes were drilled in the lid to accommodate a nitrogen inlet tube (stainless steel), cooling coil tubes (stainless steel), thermocouple tube (stainless steel), and a reagent addition tube (plastic). The reaction vessel was secured in place and purged with nitrogen. DNPOH (8.333 Kg, 55.6 moles) was placed in the reaction vessel and acetaldehyde (2.000 Kg, 45.5 moles) was added through the reagent addition tube by pressurizing the acetaldehyde bottle with nitrogen and pumping the acetaldehyde through the tube into the reaction vessel. A nitrogen blanket was maintained at all times within the reaction vessel. The DNPOH and acetaldehyde were blended by agitation with the cooling coils and cooled to 37° F. (2.8° C). $BF_3$.etherate (4.000 Kg, 28.2 moles) was carefully added the same way as the acetaldehyde to the agitated solution. 110 g of $BF_3$.etherate was added initially and the exotherm caused the temperature to rise to 69° F. (20.6° C). The reaction solution was cooled to 50° F. (10° C.), and an additional 1460 g of $BF_3$.etherate was added. The solution temperature rose to 52° F. (11.1° C.) during this addition. The reaction solution was then cooled to 46° F. (7.8° C.), and the remaining $BF_3$.etherate was added at a rate of about 328 ml/minute.

The reaction was quenched by pouring the reaction solution into a larger vessel containing 4 gallons of water. The reaction solution was then washed with 7 gallons of 5 weight percent NaOH solution. 15 gallons of MTBE were added, and the mixture was stirred vigorously for one-half hour. The aqueous layer was removed, and the organic layer was then washed with an additional 7 gallons of 5 weight percent NaOH, followed by three 4.5 gallon $H_2O$ washes. The organic layer was dried with $MgSO_4$. The MTBE was evaporated at 40° C. and less than 127 mm Hg, leaving 6.0 Kg (64% yield) BDNPA.

EXAMPLE 3

Bis(2,2-dinitropropyl)acetal is synthesized according to the procedure of Example 1 except that the acid catalyst is sulfuric acid instead of $BF_3.O(Et)_2$. In this example, 1 ml of concentrated (96%–98%) sulfuric acid is used.

EXAMPLE 4

Bis(2,2-dinitropropyl)acetal is synthesized according to the procedure of Example 1 except that the acetaldehyde source is acetal instead of acetaldehyde. In this example, 0.83 g (7.0 mmole) of acetal is used. Thus, a slight stoichiometric excess of acetal is used relative to the 2,2-dinitropropanol.

EXAMPLE 5

Bis(2,2-dinitropropyl)acetal is synthesized according to the procedure of Example 1 except that the acetaldehyde source is metaldehyde instead of acetaldehyde and the acid catalyst is sulfuric acid instead of $BF_3.O(Et)_2$. In this example, 2 ml of sulfuric acid are used. Also in this example, 0.48 g of metaldehyde is used.

EXAMPLE 6

Bis(2,2-dinitropropyl)acetal (BDNPA) is synthesized according to the procedure of Example 1, except that the 2,2-dinitropropanol and the acetaldehyde are mixed in a reaction vessel containing 4 ml hexane. The hexane is immiscible with the reaction solution and does not participate in the reaction. The hexane helps distribute heat and maintain temperature control. The hexane is removed from the final BDNPA product during evaporation of the polar organic solvent, MTBE.

EXAMPLE 7

Bis(2,2-dinitropropyl)acetal (BDNPA), synthesized according to the procedure of Example 2 without further purification, was mixed with BDNPF in a 50:50 weight ratio. The BDNPA/BDNPF mixture was tested to determine its purity according to military specifications. The mixture's density was found to be 1.38 g/cc, within the military specification range of 1.38 to 1.40 g/cc. The mixture's refractive index was measured to be 1.4635, within the military specification range of 1,462 to 1,464. Finally, the mixture was subjected to the acid aging test and had a result of 0.36 g KOH/g BDNPA, below the military specification upper limit of 0.5 g KOH/g BDNPA.

From the foregoing, it will be appreciated that the present invention provides a method for synthesizing usable BDNPA which does not use chlorinated solvents and which avoids further purification steps.

The present invention may be embodied in other specific forms without departing from its essential characteristics. The described embodiments are to be considered in all respects only as illustrative and not restrictive. The scope of the invention is, therefore, indicated by the appended claims rather than by the foregoing description.

The claimed invention is:

1. A process of synthesizing bis(2,2-dinitropropyl)-acetal (BDNPA) comprising the steps of:
    (a) mixing 2,2-dinitropropanol with a stoichiometric excess of an acetaldehyde source to form a reaction solution;
    (b) adding an acid catalyst to the reaction solution, wherein said acid catalyst participates in the process as a catalyst or dehydration agent and not as a combinatorial reagent, wherein the reaction solution is maintained at a temperature in the range from about −30° C. to 30° C. during said adding step and wherein the reaction solution is agitated during said adding step;
    (c) quenching the reaction solution with water to facilitate removal of soluble reactants and byproducts from the reaction solution;
    (d) washing the reaction solution with an aqueous hydroxide solution having a hydroxide ion concentration sufficient to neutralize acid formed during the quenching step and to solubilize unreacted 2,2-dinitropropanol;
    (e) extracting BDNPA product with methyl tert-butyl ether (MTBE); and
    (f) evaporating the organic solvent to yield usable BDNPA product without further purification, wherein the resulting yield is at least 50% based on the starting quantity of 2,2-dinitropropanol, said evaporating step occurring at a temperature less than 60° C. and at a pressure of less than 150 mm Hg.

2. A process of synthesizing BDNPA as defined in claim 1, wherein the reaction solution is maintained at a temperature in the range from about −10° C. to 10° C. during acid catalyst addition.

3. A process of synthesizing BDNPA as defined in claim 1, wherein the reaction solution is maintained at a temperature in the range from about −5° C. to 5° C. during acid catalyst addition.

4. A process of synthesizing BDNPA as defined in claim 1, wherein the acetaldehyde source is selected from acetaldehyde, paraldehyde, metaldehyde, and acetal.

5. A process of synthesizing BDNPA as defined in claim 1, wherein the aqueous hydroxide solution has a hydroxide concentration in the range from 1% to 25%, by weight.

6. A process of synthesizing BDNPA as defined in claim 1, wherein aqueous hydroxide solution is prepared from a hydroxide salt selected from NaOH, KOH, and LiOH.

7. A process of synthesizing BDNPA as defined in claim 1, wherein the acid catalyst is a Lewis acid catalyst selected from $BF_3BF_3$.etherate, $BCl_3$, $BBr_3$, $SnF_4$, $SnCl_4$, $SnBr_4$, $TiCl_3$, $TiCl_4$, $TiBr_3$, and $TiBr_4$.

8. A process of synthesizing BDNPA as defined in claim 1, wherein the acid catalyst is a protic acid catalyst selected from $H_2SO_4$, HCl, $H_3PO_4$, and HBr.

9. A process of synthesizing BDNPA as defined in claim 1, wherein the evaporating step occurs at a temperature less than 50° C. and at a pressure of less than 20 mm Hg.

10. A process of synthesizing BDNPA as defined in claim 1, wherein the 2,2-dinitropropanol and acetaldehyde source reaction solution is further mixed with an immiscible organic solvent which does not contain chlorine.

11. A process of synthesizing BDNPA as defined in claim 1, wherein the washing step occurs before the extracting step.

12. A process of synthesizing BDNPA as defined in claim 1, wherein the washing step occurs after the extracting step.

13. A process of synthesizing bis(2,2-dinitropropyl)-acetal (BDNPA) comprising the steps of:

(a) mixing 2,2-dinitropropanol with an acetaldehyde source to form a reaction solution, wherein the acetaldehyde source is selected from acetaldehyde, paraldehyde, metaldehyde, and acetal, and wherein a stoichiometric excess of acetaldehyde source is mixed with 2,2-dinitropropanol, wherein the reaction solution consists essentially of the 2,2-dinitropropanol and acetaldehyde source mixture;

(b) adding an acid catalyst to the reaction solution, wherein said acid catalyst participates in the process as a catalyst or dehydration agent and not as a combinatorial reagent, wherein the reaction solution is maintained at a temperature in the range from about −30° C. to 30° C. during said adding step and wherein the reaction solution is agitated during said adding step;

(c) quenching the reaction solution with water to facilitate removal of soluble reactants and byproducts from the reaction solution;

(d) washing the reaction solution with an aqueous hydroxide solution prepared from a hydroxide salt selected from NaOH, KOH, and LiOH, wherein said aqueous hydroxide solution has a hydroxide concentration in the range from 1% to 25%, by weight, and wherein said sufficient hydroxide solution is added to the reaction solution to neutralize any acid formed during the quenching step and to solubilize unreacted 2,2-dinitropropanol and other aqueous soluble byproducts in the reaction solution;

(e) extracting BDNPA product with methyl tert-butyl ether (MTBE);

(f) rinsing the BDNPA product with pure water to remove any remaining soluble reactants or byproducts; and (g) evaporating the organic solvent to yield usable BDNPA product without further purification, wherein the resulting yield is at least 60% based on the starting quantity of 2,2-dinitropropanol, said evaporating step occurring at a temperature less than 60° C. and at a pressure of less than 150 mm Hg.

14. A process of synthesizing BDNPA as defined in claim 13, wherein the reaction solution is maintained at a temperature in the range from about −10° C. to 10° C. during acid catalyst addition.

15. A process of synthesizing BDNPA as defined in claim 13, wherein the reaction solution is maintained at a temperature in the range from about −5° C. to 5° C. during acid catalyst addition.

16. A process of synthesizing BDNPA as defined in claim 13, wherein the acid catalyst is a Lewis acid catalyst selected from $BF_3$, $BF_3$.etherate, $BCl_3$, $BBr_3$, $SnF_4$, $SnCl_4$, $SnBr_4$, $TiCl_3$, $TiCl_4$, $TiBr_3$, and $TiBr_4$.

17. A process of synthesizing BDNPA as defined in claim 13, wherein the acid catalyst is a protic acid catalyst selected from $H_2SO_4$, HCl, $H_3PO_4$, and HBr.

18. A process of synthesizing BDNPA as defined in claim 13, wherein the 2,2-dinitropropanol and acetaldehyde source reaction solution is further mixed with an immiscible organic solvent which does not contain chlorine.

19. A process of synthesizing BDNPA as defined in claim 13, wherein the washing step occurs before the extracting step.

20. A process of synthesizing BDNPA as defined in claim 13, wherein the washing step occurs after the extracting step.

* * * * *